United States Patent
Kajanto (10) Patent No.: US 10,981,135 B2
(45) Date of Patent: *Apr. 20, 2021

(54) TREATING CATALYTICALLY OXIDIZED NANOFIBRILLAR CELLULOSE HYDROGEL

(71) Applicant: UPM-KYMMENE CORPORATION, Helsinki (FI)

(72) Inventor: Isko Kajanto, Espoo (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 308 days.

This patent is subject to a terminal disclaimer.

(21) Appl. No.: 15/538,074

(22) PCT Filed: Dec. 21, 2015

(86) PCT No.: PCT/FI2015/050916
§ 371 (c)(1),
(2) Date: Jun. 20, 2017

(87) PCT Pub. No.: WO2016/102764
PCT Pub. Date: Jun. 30, 2016

(65) Prior Publication Data
US 2017/0348663 A1    Dec. 7, 2017

(30) Foreign Application Priority Data
Dec. 22, 2014 (FI) .................... 20146138

(51) Int. Cl.
| | | |
|---|---|---|
| *A61K 8/73* | (2006.01) | |
| *B01J 13/00* | (2006.01) | |
| *A61K 8/04* | (2006.01) | |
| *A61L 2/00* | (2006.01) | |
| *A61L 2/26* | (2006.01) | |

(52) U.S. Cl.
CPC .......... *B01J 13/0069* (2013.01); *A61K 8/042* (2013.01); *A61K 8/731* (2013.01); *A61L 2/0023* (2013.01); *A61L 2/26* (2013.01); *B01J 13/0065* (2013.01); *A61L 2202/21* (2013.01)

(58) Field of Classification Search
CPC ....... A61K 31/717; A61K 8/042; A61K 8/731
USPC .................................................. 536/124, 56
See application file for complete search history.

(56) References Cited

U.S. PATENT DOCUMENTS 9,809,655 B2 *  11/2017   Laukkanen ............. C08B 15/04

FOREIGN PATENT DOCUMENTS

| EP | 2236545 A1 | 10/2010 |
|---|---|---|
| EP | 2386683 A1 | 11/2011 |
| EP | 2529942 A1 | 12/2012 |
| WO | 2012056109 A2 | 5/2012 |
| WO | 2012107642 A1 | 8/2012 |
| WO | 2012168562 A1 | 12/2012 |
| WO | 2013072563 A1 | 5/2013 |
| WO | 2014091086 A1 | 6/2014 |
| WO | 2014184442 A1 | 11/2014 |

OTHER PUBLICATIONS

Madhushree Bhattacharya et al., "Nanofibrillar cellulose hydrogel promotes three-dimensional liver cell culture", Journal of Controlled Release, vol. 164, No. 3, Dec. 1, 2012.
Yan-Ru Lou et al., "The Use of Nanofibrillar Cellulose Hydrogel As a Flexible Three-Dimensional Model to Culture Human Pluripotent Stem Cells", Stem Cells and Development, vol. 23, No. 4, Feb. 15, 2014.
Malinen Melina M. et. al., "Differentiation of liver progenitor cell line to functional organotypic cultures in 3D nanofibrillar cellulose and hyaluronan-gelatin hydrogels", Biomaterials, vol. 35, No. 19, Apr. 1, 2014.
Search Report from Patent Application No. 20146138 dated Apr. 21, 2015.
International Search Report from International Application No. PCT/FI2015/050916 dated Mar. 24, 2016.
International Preliminary Report on Patentability from International Application No. PCT/FI2015/050916 dated Mar. 9, 2017.

* cited by examiner

*Primary Examiner* — Shaojia A Jiang
*Assistant Examiner* — Everett White
(74) *Attorney, Agent, or Firm* — Nixon Peabody LLP (57) ABSTRACT

The invention relates to a method for treating a nanofibrillar cellulose hydrogel, wherein the method comprises the steps of: providing a nanofibrillar cellulose hydrogel, wherein the nanofibrillar cellulose is oxidized nanofibrillar cellulose, wherein the oxidation has been carried out through N-oxyl mediated catalytic oxidation of cellulose-based raw material, and has at most 50 μmol of aldehyde groups per gram of dry nanofibrillar cellulose; and subjecting the nanofibrillar cellulose hydrogel to a heat treatment.

18 Claims, 1 Drawing Sheet

TREATING CATALYTICALLY OXIDIZED NANOFIBRILLAR CELLULOSE HYDROGEL

CROSS-REFERENCE TO RELATED APPLICATIONS

This application is a U.S. National Stage of International Application No. PCT/FI2015/050916, filed on Dec. 21, 2015, which claims priority to Finnish Patent No. 20146138, filed Dec. 22, 2014, the contents of each of which are incorporated herein by reference in their entireties.

FIELD OF THE INVENTION

The invention relates to a method for treating nanofibrillar cellulose hydrogel. The invention further relates a nanofibrillar cellulose hydrogel, to a system for treating a nanofibrillar cellulose hydrogel, and to the use of the nanofibrillar cellulose hydrogel.

BACKGROUND OF THE INVENTION

A nanofibrillar cellulose hydrogel has been found use in different applications such as in cosmetics and pharmaceuticals as well as in cell growth medium. However, the use thereof in cosmetic or pharmaceutical products or devices put challenges on ensuring that the hydrogel is aseptic or sterile as well as on its other properties that may be affected by the used sterilization procedure.

Generally, sterilization efficiency is defined as the ability to remove or destroy all forms of microbial life, including viruses, bacteria and fungi, under vegetative forms or spores. However, since absolute sterility cannot be verified, the statistical definition of sterility is used in practice, by using the security assurance level (SAL), defined as "the probability of a single viable micro-organism occurring in or on a product after sterilization". The worldwide accepted definition of sterility of medical devices is defined as the chance of finding a viable organism in or on a medical device to be at most 1 in 1000000 or an SAL of at most $10^{-6}$.

The number of viable micro-organisms in nanofibrillar cellulose hydrogel can be reduced or eliminated by subjecting the hydrogel to autoclaving for 20 minutes at a temperature of 121° C. Autoclaving, however, has some challenges as it affects the properties, such as viscosity, of the hydrogel.

The inventors have therefore recognized the need for a method to produce a nanofibrillar cellulose hydrogel such that it is suitable for further applications.

Purpose of the Invention

The purpose of the invention is to provide a new type of method for treating nanofibrillar cellulose hydrogel. Further the purpose of the invention is to provide a new type of nanofibrillar cellulose hydrogel and new uses of nanofibrillar cellulose hydrogel. Further the purpose of the invention is to provide a new system for treating nanofibrillar cellulose hydrogel.

SUMMARY

A method for treating a nanofibrillar cellulose hydrogel is disclosed. The method comprises providing a nanofibrillar cellulose hydrogel having a dry-matter content of at least 0.6weight-%, wherein the nanofibrillar cellulose is oxidized nanofibrillar cellulose, wherein the oxidation has been carried out through N-oxyl mediated catalytic oxidation of cellulose-based raw material, and has at most 50 µmol of aldehyde groups per gram of dry nanofibrillar cellulose. The method further comprises subjecting the nanofibrillar cellulose hydrogel to a heat treatment, wherein the heat treatment comprises keeping the nanofibrillar cellulose hydrogel at a predetermined temperature within the range of 100-150° C., for a period of time in the range of 1 second to 180 minutes, wherein the predetermined temperature and the period of time are chosen such that the number of viable micro-organisms in the nanofibrillar cellulose hydrogel is reduced. The nanofibrillar cellulose hydrogel after the heat treatment has a viscosity of 2000-40000 mPa·s as measured at a 0.8% (w/w) concentration of the nanofibrillar cellulose in water with a Brookfield viscometer at a temperature of 20° C., with a vane spindle and a measuring speed of 10 rpm, the viscosity of the nanofibrillar cellulose hydrogel after the heat treatment differing at most by 30% from the viscosity of the nanofibrillar cellulose hydrogel before the heat treatment.

A nanofibrillar cellulose hydrogel is disclosed. The nanofibrillar cellulose is oxidized nanofibrillar cellulose, wherein the oxidation has been carried out through N-oxyl mediated catalytic oxidation of cellulose-based raw material, wherein the nanofibrillar cellulose hydrogel has been subjected to a heat treatment comprising keeping the nanofibrillar cellulose hydrogel at a predetermined temperature within the range of 100-150° C., for a period of time in the range of 1 second to 180 minutes, the nanofibrillar cellulose hydrogel having at most 50 µmol of aldehyde groups per gram of dry nanofibrillar cellulose, and wherein the nanofibrillar cellulose hydrogel contains no colony-forming units of a viable micro-organism per gram of the nanofibrillar cellulose hydrogel, as measured by culturing on a growth medium, and has a viscosity of 2000-40000 mPa·s as measured at a 0.8% (w/w) concentration of the nanofibrillar cellulose in water with a Brookfield viscometer at a temperature of 20° C., with a vane spindle and a measuring speed of 10 rpm, the viscosity of the nanofibrillar cellulose hydrogel after the heat treatment differing at most by 30% from the viscosity of the nanofibrillar cellulose hydrogel before the heat treatment.

A nanofibrillar cellulose hydrogel for use in therapy is disclosed. The nanofibrillar cellulose is oxidized nanofibrillar cellulose, wherein the oxidation has been carried out through N-oxyl mediated catalytic oxidation of cellulose-based raw material, and wherein the nanofibrillar cellulose hydrogel has been subjected to a heat treatment comprising keeping the nanofibrillar cellulose hydrogel at a predetermined temperature within the range of 100-150° C., for a period of time in the range of 1 second to 180 minutes, the nanofibrillar cellulose hydrogel having at most 50 µmol of aldehyde groups per gram of dry nanofibrillar cellulose, and wherein the nanofibrillar cellulose hydrogel contains at most $10^2$ colony-forming units of a viable micro-organism per gram of the nanofibrillar cellulose hydrogel, and has a viscosity of 2000-40000 mPa·s as measured at a 0.8% (w/w) concentration of the nanofibrillar cellulose in water with a Brookfield viscometer at a temperature of 20° C., with a vane spindle and a measuring speed of 10 rpm, the viscosity of the nanofibrillar cellulose hydrogel after the heat treatment differing at most by 30% from the viscosity of the nanofibrillar cellulose hydrogel before the heat treatment.

BRIEF DESCRIPTION OF THE DRAWINGS

The accompanying drawing, which is included to provide a further understanding of the invention and constitutes a part of this specification, illustrate one embodiment of the invention and together with the description helps to explain the principles of the invention. In the drawing:

FIG. 1 is an illustration of the system according to one embodiment of the present invention.

DETAILED DESCRIPTION OF THE INVENTION

The present invention relates to a method for treating a nanofibrillar cellulose hydrogel, wherein the method comprises the steps of: providing a nanofibrillar cellulose hydrogel, wherein the nanofibrillar cellulose is oxidized nanofibrillar cellulose, wherein the oxidation has been carried out through N-oxyl mediated catalytic oxidation of cellulose-based raw material, and has at most 50 µmol of aldehyde groups per gram of dry nanofibrillar cellulose; and subjecting the nanofibrillar cellulose hydrogel to a heat treatment, wherein the heat treatment comprises keeping the nanofibrillar cellulose hydrogel at a predetermined temperature within the range of 100-150° C. for a period of time in the range of 1 second to 180 minutes, wherein the predetermined temperature and the period of time are chosen such that the number of viable micro-organisms in the nanofibrillar cellulose hydrogel is reduced.

The present invention relates to a method for treating a nanofibrillar cellulose hydrogel, wherein the method comprises the steps of: providing a nanofibrillar cellulose hydrogel, wherein the nanofibrillar cellulose is oxidized nanofibrillar cellulose, wherein the oxidation has been carried out through N-oxyl mediated catalytic oxidation of cellulose-based raw material, and has at most 50 µmol of aldehyde groups per gram of dry nanofibrillar cellulose; and subjecting the nanofibrillar cellulose hydrogel to a heat treatment, wherein the heat treatment comprises keeping the nanofibrillar cellulose hydrogel at a predetermined temperature within the range of 100-150° C., and at a predetermined pressure, which is higher than vapour pressure of water in the nanofibrillar cellulose hydrogel, for a period of time in the range of 1 second to 180 minutes, wherein the predetermined temperature, the predetermined pressure, and the period of time are chosen such that the number of viable micro-organisms in the nanofibrillar cellulose hydrogel is reduced.

The present invention further relates to a system for treating a nanofibrillar cellulose hydrogel, wherein the system comprises: a fibrillation unit, which is configured to fibrillate oxidized cellulose-based raw material, wherein the oxidation has been carried out through N-oxyl mediated catalytic oxidation of cellulose-based raw material, to provide a nanofibrillar cellulose hydrogel, wherein the nanofibrillar cellulose is oxidized nanofibrillar cellulose having at most 50 µmol of aldehyde groups per gram of dry nanofibrillar cellulose; and a heating apparatus for subjecting the nanofibrillar cellulose hydrogel to a heat treatment, wherein the heating apparatus is configured to keep the nanofibrillar cellulose hydrogel at a predetermined temperature within the range of 100-150° C. for a period of time in the range of 1 second to 180 minutes, wherein the pre-determined temperature and the period of time are chosen such that the number of viable micro-organisms in the nanofibrillar cellulose hydrogel is reduced.

The present invention further relates to a system for treating a nanofibrillar cellulose hydrogel, wherein the system comprises: a fibrillation unit, which is configured to fibrillate oxidized cellulose-based raw material, wherein the oxidation has been carried out through N-oxyl mediated catalytic oxidation of cellulose-based raw material, to provide a nanofibrillar cellulose hydrogel, wherein the nanofibrillar cellulose is oxidized nanofibrillar cellulose having at most 50 µmol of aldehyde groups per gram of dry nanofibrillar cellulose; and a heating apparatus for subjecting the nanofibrillar cellulose hydrogel to a heat treatment, wherein the heating apparatus is configured to keep the nanofibrillar cellulose hydrogel at a predetermined temperature within the range of 100-150° C., and at a predetermined pressure, which is higher than vapour pressure of water in the nanofibrillar cellulose hydrogel, for a period of time in the range of 1 second to 180 minutes, wherein the pre-determined temperature, the predetermined pressure, and the period of time are chosen such that the number of viable micro-organisms in the nanofibrillar cellulose hydrogel is reduced.

In one embodiment, the system for treating a nanofibrillar cellulose hydrogel comprises:
an oxidation unit, which is configured to subject cellulose-based raw material to a oxidation process through N-oxyl mediated catalytic oxidation;
a reduction unit, which is configured to subject the oxidized cellulose-based raw material to a reduction process;
a fibrillation unit, which is configured to fibrillate oxidized cellulose-based raw material, wherein the oxidation has been carried out through N-oxyl mediated catalytic oxidation of cellulose-based raw material, to provide a nanofibrillar cellulose hydrogel, wherein the nanofibrillar cellulose is oxidized nanofibrillar cellulose having at most 50 µmol of aldehyde groups per gram of dry nanofibrillar cellulose; and
a heating apparatus for subjecting the nanofibrillar cellulose hydrogel to a heat treatment, wherein the heating apparatus is configured to keep the nanofibrillar cellulose hydrogel at a predetermined temperature within the range of 100-150° C. for a period of time in the range of 1 second to 180 minutes, wherein the pre-determined temperature, and the period of time are chosen such that the number of viable micro-organisms in the nanofibrillar cellulose hydrogel is reduced.

The present invention further relates to the use of a heat treatment for reducing the number of viable micro-organisms in a nanofibrillar cellulose hydrogel, wherein the nanofibrillar cellulose is oxidized nanofibrillar cellulose, wherein the oxidation has been carried out through N-oxyl mediated catalytic oxidation of cellulose-based raw material, and has at most 50 µmol of aldehyde groups per gram of dry nanofibrillar cellulose, and wherein the heat treatment comprises keeping the nanofibrillar cellulose hydrogel at a predetermined temperature within the range of 100-150° C. for a period of time in the range of 1 second to 180 minutes, wherein the pre-determined temperature and period of time are chosen such that the number of viable micro-organisms in the nanofibrillar cellulose hydrogel is reduced.

The present invention further relates to the use of a heat treatment for reducing the number of viable micro-organisms in a nanofibrillar cellulose hydrogel, wherein the nanofibrillar cellulose is oxidized nanofibrillar cellulose, wherein the oxidation has been carried out through N-oxyl mediated catalytic oxidation of cellulose-based raw material, and has at most 50 µmol of aldehyde groups per gram of dry nanofibrillar cellulose, and wherein the heat treatment comprises keeping the nanofibrillar cellulose hydrogel at a predetermined temperature within the range of 100-150° C., and at a predetermined pressure, which is higher than vapour pressure of water in the nanofibrillar cellulose hydrogel, for a period of time in the range of 1 second to 180 minutes, wherein the pre-determined temperature, the predetermined pressure and period of time are chosen such that the number of viable micro-organisms in the nanofibrillar cellulose hydrogel is reduced.

The operating pressure or the predetermined pressure is to be selected so that the desired or predetermined temperature is reached and the nanofibrillar cellulose hydrogel is not boiling in the used temperature. Nanofibrillar cellulose itself is not a volatile component and it does not boil. In one embodiment, the predetermined pressure is higher than vapor pressure of water in the nanofibrillar cellulose hydrogel in the predetermined temperature.

In one embodiment, the heat treatment is carried out such that the dry-matter content of the nanofibrillar cellulose hydrogel remains essentially constant during the heat treatment. In one embodiment, the heat treatment is carried out such that the dry-matter content of the nanofibrillar cellulose hydrogel changes at most 5 weight-%, or at most 3 weight-%, or at most 1 weight-%, during the heat treatment. The heat treatment should be carried out such that the nanofibrillar cellulose hydrogel is not allowed to dry to an adverse extent during the heat treatment.

In one embodiment the heat treatment is carried out in an autoclave. In one embodiment the heat treatment is carried out in at least one heat exchanger. In one embodiment, the heating apparatus is an autoclave. In one embodiment, the heating apparatus is a heat exchanger.

In one embodiment, the step of providing a nanofibrillar cellulose hydrogel comprises providing oxidized nanofibrillar cellulose, which has at most 40 µmol, or at most 30 µmol, or at most 20 µmol, or at most 10 µmol, of aldehyde groups per gram of dry nanofibrillar cellulose.

In one embodiment, the nanofibrillar cellulose in the nanofibrillar cellulose hydrogel is oxidized and has at most 50 µmol, or at most 40 µmol, or at most 30 µmol, or at most 20 µmol, or at most 10 µmol, of aldehyde groups per gram of dry nanofibrillar cellulose.

In one embodiment the step of providing nanofibrillar cellulose hydrogel comprises providing oxidized nanofibrillar cellulose containing essentially no aldehyde groups.

The amount of aldehyde groups present in the oxidized nanofibrillar cellulose can be determined based on the amount of carboxylic acid present in the oxidized cellulose-based raw material, e.g. in pulp. E.g. fibrillation of the cellulose-based raw material does not essentially change the amount of aldehyde groups, i.e. the amount of aldehyde groups is essentially the same in the oxidized cellulose-based raw material and in the oxidized nanofibrillar cellulose.

For the determination of the C(6)-carboxyl and/or -aldehyde contents different manners can be used.

The amount of carboxyl groups can be determined by conductometric titration and then calculated by converting the thus obtained charge value into µmol/g. One method of performing the conductometric titration and determination of the COOH content is described by S. Katz in "Svensk Papperstidning" 6/1984, p. 48.

Another method for determining the content of C(6)-aldehyde/carboxy groups in fibre material is the Blumenkrantz method (N. Blumenkrantz and G.Asboe-Hansen, Anal. Biochem. 1973, 54, 10 484). This method is based on the colorimetric determination of a pink compound arising when a decomposition product of the uronic acid polymer (C6-carboxy cellulose) reacts with 3-hydroxybiphenyl.

Another method for the determination of C(6)-aldehyde contents involves the conversion of the oxidized material with hydroxylamine hydrochloride to the oxim. The C(6) oxim displays a distinct signal in 13C NMR spectra.

Another method for determining the aldehyde content involves the hydroxylamine method: to a sample of 25 ml water containing 1 g of aldehyde-containing fibres, 0.20 g hydroxylammonium chloride (e.g. obtainable from E. Merck, Germany) is added which results in a gradual decrease of the pH value. The reaction mixture is heated for at least 3 hours at 40° C. The amount of HCl released is then titrated with 0.1 M NaOH (Titrisol, obtainable from Merck, Germany) up to end point of pH 3.4 and the consumed NaOH is recalculated to µmol aldehyde/g fibres.

In a non-restricting example of determining the amount of aldehyde groups in oxidized nanofibrillar cellulose, the use of a two-step oxidation process can be used as a basis. The amount of aldehyde groups after N-oxyl mediated catalytic oxidation can be received by reducing the amount of carboxylic acid after the first oxidation step (phase-1) from the result obtained after the second oxidation step, where residual aldehydes are converted to carboxylic acids (phase-2). The amount of aldehyde groups can thus be calculated based on the following:

Aldehyde groups (mmol/g of dry nanofibrillar cellulose)=(amount of COOH from phase-2 (mmol/g of dry pulp))−(amount of COOH from phase 1 (mmol/g of dry pulp))

As an example of calculating the number of aldehyde groups the following is presented: During phase-1 bleached birch pulp is oxidized. Firstly TEMPO is mixed with a $ClO_2$ water solution in a closed vessel. The pulp is mixed with water (pulp consistency of 1-4%) and transferred to a Büchi reactor (mixing, temperature 25-50° C., volume of pulp solution 1-1.2 $dm^3$). The activated TEMPO solution and NaClO are added to the Büchi reactor. The pH is adjusted by 1 M NaOH and automatic titrator after rapid pH decrease at the beginning of the oxidation. The oxidation rate is measured by active chlorine titration until all of the HOCl is consumed. The pulp is washed through wire cloth. The carboxylate content is analyzed from washed pulp by conductometric titration. Then phase-2 is carried out in order to convert residual aldehydes to carboxylates. The oxidized pulp suspension at a 1% consistency, after washing or subsequently without washing, is adjusted to pH 2 by 1 M HCl. Then $NaClO_2$ is added to the solution (1 mM final concentration) and oxidation of the aldehydes (conversion) is carried out in Büchi reactor (2 hours, 50° C.). Then the pulp is washed and analyzed. The carboxylate content can be analyzed from washed pulp samples by conductometric titration. Conductometric titration can be carried out in the following manner: The pulp is converted to a protonated form prior to the titration. First, the pH of the pulp suspension is adjusted to 2 with 1M HCl. The solution is left to stabilize for 0.5 hours after which the pulp is washed with water until the conductivity of the slurry is less than 5 µS/cm. Approximately 1 g (dry matter content) of pulp is weighted in a 600 ml Erlenmeyer flask. Carbon dioxide is removed by a vacuum from the purified water. The carbon dioxide-free water is used both during the titration and the reagent solution preparation. The pulp sample is dispersed in 498.5 ml of water. Then, 1 ml of 0.1 M HCl and 0.5 ml of 0.5 M NaCl are added to the Erlenmeyer flask. Titration is executed under argon gas atmosphere using an automatic titrator (Metrohm 751 GPD Titrino) together with Tiamo 1.2.1. software.

The inventors surprisingly found out that a nanofibrillar cellulose hydrogel, wherein the nanofibrillar cellulose is oxidized nanofibrillar cellulose, which has been oxidized in order to provide at most 50 µmol, or at most 40 µmol, or at most 30 µmol, or at most 20 µmol, or at most 10 µmol, of aldehyde groups per gram of dry nanofibrillar cellulose enabled the hydrogel to withstand the adverse effect that e.g. autoclaving is known to have on nanofibrillar cellulose hydrogel. When subjecting this kind of nanofibrillar cellulose hydrogel to a heat treatment, e.g. in an autoclave, the amount of viable micro-organism could be reduced while e.g. the viscosity of the hydrogel was not adversely affected in a usually noticed extent.

The expression "hydrogel" or "nanofibrillar cellulose hydrogel" should be understood in this specification, unless otherwise stated, as referring to an aqueous dispersion of nanofibrillar cellulose having a continuous or discontinuous gel structure. By a "discontinuous" gel structure is to be understood a continuous gel, which is broken into pieces. The hydrogel can be formed by combining nanofibrillar cellulose with e.g. water, buffer solution, cell culture medium or any other aqueous solution optionally supplemented with additives. The storage modulus (G') value of the nanofibrillar cellulose hydrogel is greater than its loss modulus (G") value, i.e. the loss tangent is below 1 at least up to strain value 10%. The storage modulus G', loss modulus G" and loss tangent (G"/G') of nanofibrillar cellulose hydrogels can be determined with the frequency sweep in dynamic oscillation mode of the rheometer (strain 1% and 10%, frequency 0.1-100, temperature 25° C., pH 7.0). The stress sweep is measured in a shear stress range of 0,001-100 Pa at the frequency 0.1 Hz, and at a temperature of 25° C. and at pH 7. For characterizing the gel forming capacity of a nanofibrillar cellulose the measurement is performed in 0.5 weight-%, 1% strain, frequency of 0.1 Hz. For determining whether a certain material is a gel, i.e. whether its loss tangent is below 1, the measurement is performed in the same way except in the material's consistency. The storage modulus of oxidized nanofibrillar celluloses may vary from 1 to 100 Pa, or from 2 to 50 Pa, or from 5 to 20 Pa, in water at 0.5 weight-% concentration.

The expression "nanofibrillar cellulose" or "NFC" should be understood in this specification, unless otherwise stated, as referring to a collection of isolated cellulose nanofibrils (CNF) or nanofibril bundles derived from cellulose-based raw material.

The fibrils can be isolated from cellulose based raw material. The expression "cellulose-based raw material" should be understood in this specification, unless otherwise stated, as referring to any fibre material source that contains cellulose and from which nanofibrillar cellulose can be produced.

In one embodiment, the cellulose-based raw material is based on any plant material that contains cellulose. Plant material may be wood. Wood can be from softwood tree such as spruce, pine, fir, larch, douglas-fir or hemlock, or from hardwood tree such as birch, aspen, poplar, alder, eucalyptus or acacia, or from a mixture of softwoods and hardwoods. Non-wood material can be from agricultural residues, grasses or other plant substances such as straw, leaves, bark, seeds, hulls, flowers, vegetables or fruits from cotton, corn, wheat, oat, rye, barley, rice, flax, hemp, manila hemp, sisal hemp, jute, ramie, kenaf, bagasse, bamboo or reed.

Depending on the source, different polysaccharide composition may exist in the final nanofibrillar cellulose hydrogel. The nanofibrillar celluloses may contain hemicelluloses and lignin in varying amounts, depending on plant source and pulping conditions.

In one embodiment, the cellulose-based raw material does not contain substantial amounts of lignin. In one embodiment, the nanofibrillar cellulose is essentially free of lignin.

Nanofibrils typically have a high aspect ratio. The length might exceed one micrometer while the diameter is typically below 200 nm. The smallest nanofibrils are similar to so called elementary fibrils, which are typically 2-12 nm in diameter. The dimensions of the fibrils or fibril bundles are dependent on raw material and disintegration method. Oxidized nanofibrillar cellulose has typically smaller diameters, the number average diameters ranging from 1 to 100 nm, or from 2 to 20 nm, or from 2 to 10 nm. Fibril thickness and width distribution may be measured by image analysis of images from a field emission scanning electron microscope (FE-SEM), a transmission electron microscope (TEM), such as a cryogenic transmission electron microscope (cryo-TEM), or an atomic force microscope (AFM).

Nanofibrillar cellulose is characterized by very high water retention values, a high degree of chemical accessibility and the ability to form stable gels, hydrogels, in water or other polar solvents. Nanofibrillar cellulose product is typically a dense network of highly fibrillated cellulose. In an aqueous environment, a dispersion of cellulose nanofibers forms a viscoelastic hydrogel network. The hydrogel is formed at relatively low concentrations of for example 0.05-0.2% w/w by dispersed and hydrated entangled fibrils.

In one embodiment, the step of providing a nanofibrillar cellulose hydrogel comprises providing a nanofibrillar cellulose hydrogel having a dry-matter content of at least 0.6 weight-%, or at least 0.7 weight-%, or at least 0.8 weight-%, or at least 0.9 weight-%, or at least 1 weight-%. In one embodiment, the step of providing a nanofibrillar cellulose hydrogel comprises providing a nanofibrillar cellulose hydrogel having a dry-matter content of at most 4 weight-%, or at most 3 weight-%, or at most 2 weight-%.

In one embodiment, the nanofibrillar cellulose hydrogel to be subjected to heat treatment has a dry-matter content of at least 0.6 weight-%, or at least 0.7 weight-%, or at least 0.8 weight-%, or at least 0.9 weight-%, or at least 1 weight-%. In one embodiment, the nanofibrillar cellulose hydrogel to be subjected to heat treatment has a dry-matter content of at most 4 weight-%, or at most 3 weight-%, or at most 2 weight-%.

In one embodiment, the nanofibrillar cellulose hydrogel to be subjected to heat treatment has a dry-matter content of 0.6-4 weight-%, or 0.7-3 weight-%, or 0.8-2 weight-%.

The nanofibrillar cellulose is oxidized nanofibrillar cellulose, wherein the oxidation has been carried out through N-oxyl mediated catalytic oxidation of cellulose-based raw material. The N-oxyl mediated catalytic oxidation affects the primary alcohols of cellulose and oxidizes them to aldehydes and carboxylic acids. The N-oxyl mediated catalytic oxidation can be carried out by using as a catalyst any heterocyclic nitroxyl radical capable of catalyzing selectively the oxidation of hydroxyl groups of the C-6 carbon of cellulose. In one embodiment the N-oxyl mediated catalytic oxidation is carried out through 2,2,6,6-tetramethyl-1-piperidine N-oxide, known by the abbreviation "TEMPO". Various TEMPO oxidation processes for cellulose are known in the art. Other heterocyclic nitroxyl compounds known to display selectivity in the oxidation of the hydroxyl groups of the C-6 carbon of cellulose are known and may also be included as a catalyst.

In one embodiment, the oxidation of cellulose-based raw material is carried out in a two-step process comprising a first step and a second step, wherein the first step at least partly precedes the second step.

In the first step hydroxyl groups of the C-6 carbon of cellulose in the cellulose-based raw material are oxidized. In the first step the hydroxyl groups of the C-6 carbon of cellulose in the cellulose-based raw material can be TEMPO-oxidized by using hypochlorite as oxidant. In one embodiment, oxidation in the first step is carried out by sodium hypochlorite (NaClO) as oxidant. In one embodiment, chlorine dioxide is used as activator in the first step.

In the second step the remaining aldehyde groups of cellulose in the cellulose-based raw material are oxidized to carboxylic groups. In the second step the remaining aldehyde groups of cellulose in the cellulose-based raw material can be oxidized to carboxylic groups by chlorite as oxidant. In one embodiment, oxidation in the second step is carried out by sodium chlorite ($NaCl_2$) as oxidant. In one embodiment, the pH is lower in the second step compared to the first step.

The two-step process can be carried out in a manner as is described in WO 2014091086.

In one embodiment, the oxidation is carried out in a one-step process. In the one-step process, the hydroxyl groups of the C-6 carbon of cellulose in the cellulose-based raw material are oxidized to aldehyde groups and further to carboxylic groups. The one-step process is carried out for a time needed to convert a sufficient amount of the aldehyde groups to carboxylic groups. In one embodiment, the one-step process is carried out until an amount of at most 50 µmol of aldehyde groups per gram of dry cellulose-based raw material is formed. In one embodiment, in the one-step process the hydroxyl groups of the C-6 carbon of cellulose in the cellulose-based raw material are TEMPO-oxidized by using hypochlorite as oxidant to aldehyde groups and further to carboxylic groups. In one embodiment, oxidation in the one-step process is carried out by sodium hypochlorite (NaClO) as oxidant. In one embodiment, chlorine dioxide is used as activator in the first step.

In one embodiment, the system comprises an oxidation unit, which is configured to subject cellulose-based raw material to an oxidation process through N-oxyl mediated catalytic oxidation.

In one embodiment, the system comprises a reduction unit, which is configured to subject the oxidized cellulose-based raw material to a reduction process.

In one embodiment, the heating apparatus is an autoclave. An autoclave is a pressure chamber or vessel that can be used to sterilize equipment, supplies and material. The sterilization can be carried out by subjecting the object to be treated to high pressure saturated steam at high temperature.

In one embodiment, when the system is in use, the oxidation unit subjects the cellulose-based raw material to an oxidation process through N-oxyl mediated catalytic oxidation. In one embodiment, when the system is in use, the oxidation unit oxidizes cellulose-based raw material through N-oxyl mediated catalytic oxidation. In one embodiment, when the system is in use, the reduction unit subjects the oxidized cellulose-based raw material to a reduction process. In one embodiment, when the system is in use, the fibrillation unit fibrillates the oxidized cellulose-based raw material. In one embodiment, when the system is in use, the heating apparatus keeps the nanofibrillar cellulose hydrogel at predetermined temperature within the range of 100-150° C. In one embodiment, when the system is in use, the heating apparatus keeps the nanofibrillar cellulose hydrogel at predetermined temperature within the range of 100-150° C. and at a pressure, which is higher than vapour pressure of water in the nanofibrillar cellulose hdyrogel.

In one embodiment, the step of providing a nanofibrillar cellulose hydrogel comprises fibrillating oxidized cellulose-based raw material to form nanofibrillar cellulose hydrogel. In one embodiment, providing the nanofibrillar cellulose hydrogel comprises fibrillation of cellulose-based raw material. In one embodiment, providing the nanofibrillar cellulose hydrogel comprises fibrillation of oxidized cellulose-based raw material. In one embodiment the nanofibrillar cellulose hydrogel is provided by fibrillation of cellulose pulp or refined pulp. Cellulose pulp can be used as cellulose-based raw material. Cellulose pulp can be formed by isolating cellulose fibers from raw material that contains cellulose by chemical, mechanical, thermo-mechanical, or chemithermo mechanical pulping processes, e.g. kraft pulping, sulfate pulping, soda pulping, organosolv pulping, and by conventional bleaching processes. In one embodiment fibrillation of cellulose-based raw material is carried out with a refiner, grinder, homogenizer, colloider, friction grinder, ultrasound sonicator, fluidizer such as microfluidizer, macrofluidizer or fluidizer-type homogenizer. In one embodiment of the present invention the step of pre-refining cellulose-based raw material is preceding the step of fibrillating the cellulose-based raw material.

The dimensions of the fibrils or fibril bundles of the nanofibrillar cellulose are dependent on the raw material and the fibrillation method. The term fibrillation may be used interchangeably with expression disintegration, and generally refers to disintegrating cellulose-based raw material mechanically by work applied to the fibers, where cellulose fibrils are liberated from the fibers or fiber fragments. The work may be based on various effects, like grinding, crushing or shearing, or a combination of these, or another corresponding action that delaminates the cell walls of the fibers and liberates fibrils. The energy taken by the refining work is normally expressed in terms of energy per processed raw material quantity, in units of e.g. kWh/kg, MWh/ton, or units proportional to these. The disintegration is performed at conditions wherein water is sufficiently present to prevent the formation of bonds between the fibers.

In one embodiment, the system comprises a packaging unit for packaging the treated nanofibrillar cellulose hydrogel. In one embodiment, the packaging unit is configured to package the treated nanofibrillar cellulose hydrogel. In one embodiment, the packaging unit packages the treated nanofibrillar cellulose hydrogel when in use.

In one embodiment, the pre-determined temperature and the period of time are chosen such that the nanofibrillar cellulose hydrogel is kept at a temperature for a period of time that correspond to a steam autoclave treatment carried out at a temperature of 121° C. for 20 minutes.

The person skilled in the art is capable of determining the specific period of time to be chosen for a specific predetermined temperature to reduce the number of viable micro-organisms in the nanofibrillar cellulose hydrogel. The person skilled in the art is capable of determining the specific period of time to be chosen for a specific predetermined temperature to reduce the number of viable micro-organisms in the nanofibrillar cellulose hydrogel by a factor of at least $10^2$, or at least $10^3$, or at least $10^6$, or at least $10^{12}$. As one non-restricting example, reducing the number of viable micro-organisms by heat treatment can be considered to be characterized with two functions and two parameters. The first is based on that the decay of the number of micro-organisms at a certain temperature follows the exponential decay time:

$$N(t)=N(0)e^{-Ct}$$

Then, the following parameter is defined:
DT-=decimal reduction time at temperature T
This is the time that is required to reduce the number of micro-organisms by one decade $$N_t = \frac{N_0}{10}$$

D-values depend on temperature and they are given at a certain temperature, e.g. $D_{121}$ for T=121° C. The time to reach a certain reduction in the number of viable microorganisms is denoted with a F-value. If a requirement for a reduction is 12 decades, then the F-value is $$F=12D_T$$

The other parameter indicates the dependence of the D-value on temperature. Generally, the higher the temperature is the higher is the death rate. This is defined as the z-value.

$$z = \frac{T_2 - T_1}{-\log_{10}\left(\frac{D_2}{D_1}\right)}$$

By rearranging, $D_2$ is obtained as follows:

$$D_2 = D_1 10^{\frac{T_2-T_1}{z}}$$

The efficiency of the method can be tested by using certain standard bacteria, e.g. as below indicated:

|  | Form | D | D at T | z |
|---|---|---|---|---|
| Aerobic |  |  |  |  |
| Staphylococcus aureus | Vegetative cells | 7 min | 60° C. | 9.5° C. |
| Bacillus subtilis | Bacterial spores | 3.7 min | 100° C. | 7.3° C. |
| Pseudomonas aeruginosa | Vegetative cells | 5.07 min | 55° C. |  |
| Anaerobic |  |  |  |  |
| Clostridinium sporogenes | Spores | 15 min | 110° C. | 12.9° C. |
| Fungi |  |  |  |  |
| Candida albicans |  |  |  |  |
| Aspergillus niger | Conidium | 0.45 min | 60° C. | 3.7° C. |

D and Z values for the above micro-organisms can be found in the following publications:

*Staphylococcus aureus*: Gaze J. E. (1985) The effect of oil on the heat resistance of *Staphylococcus aureus*. Food Microbiology 2: 277-283;

*Bacillus subtilis*: Serp D., von Stockar U. and Marison I. W. (2002) Immobilized Bacterial Spores for Use as Bioindicators in the Validation of Thermal Sterilization Processes. Journal of food protection 65: 1134-1141;

*Pseudomonas aeruginosa*: Spinks A. T., Dunstan R. H., Harrison T., Coombes P. and Kuczera G. (2006) Thermal inactivation of water-borne pathogenic and indicator bacteria at sub-boiling temperatures. Water Research 40: 1326-1332;

*Clostridinium sporogenes*: Cameron M. S., Leonard S. J. and Barrett E. L. (1980) Effect of Moderately Acidic pH on Heat Resistance of *Clostridium sporogenes* Spores in Phosphate Buffer and in Buffered Pea Puree. Applied and Environmental Microbiology 39(5): 943-949; and

*Aspergillus niger*: Shearer A. E. H., Mazzotta A. S., Chuyate R. and Gombas D. E. (2002) Heat resistance of Juice spoilage microorganisms. Journal of food protection 65(8): 1271-1275.

Thus, if a temperature of e.g. 135° C. is used, based on the above table the time required to obtain $F=12D_{135}$ can be estimated. Based on this the below values can be calculated:

|  | Form | $D_{135}$ | F = 12 × $D_{135}$ |
|---|---|---|---|
| Aerobic |  |  |  |
| Staphylococcus aureus | Vegetative cells | <1 sec | <1 sec |
| Bacillus subtilis | Bacterial spores | <1 sec | <1 sec |
| Pseudomonas aeruginosa | Vegetative cells | — | — |
| Anaerobic |  |  |  |
| Clostridinium sporogenes | Spores | 10 sec | 2.1 min |
| Fungi |  |  |  |
| Candida albicans |  | — | — |
| Aspergillus niger | Conidium | <1 sec | <1 sec |

In one embodiment, the heat treatment comprises keeping the nanofibrillar cellulose hydrogel at a predetermined temperature within the range of 121-145° C.

In one embodiment, the heat treatment is carried out for a period of time in the range of 15 seconds-20 minutes.

In one embodiment, the heat treatment comprises keeping the nanofibrillar cellulose hydrogel at a temperature of at least 121° C. for at least 10 minutes, or for at least 15 minutes, or for at least 20 minutes. In one embodiment, the heat treatment comprises keeping the nanofibrillar cellulose hydrogel at a temperature of at least 121° C. for at most 30 minutes, or for at most 25 minutes, or for at most 20 minutes, or for at most 15 minutes. In one embodiment, the heat treatment comprises keeping the nanofibrillar cellulose hydrogel at a temperature of at most 123° C., or at most 125° C., for at least 10 minutes, or for at least 15 minutes, or for at least 20 minutes. In one embodiment, the heat treatment comprises keeping the nanofibrillar cellulose hydrogel at a temperature of at most 123° C., or at most 125° C., for at most 30 minutes, or for at most, 25 minutes, or for at most 20 minutes, or for at most 15 minutes.

In one embodiment, the heat treatment comprises keeping the nanofibrillar cellulose hydrogel at a temperature of at least 134° C. for at least 30 seconds, or for at least 60 seconds, or for at least 2 minutes, or for at least 3 minutes. In one embodiment, the heat treatment comprises keeping the nanofibrillar cellulose hydrogel at a temperature of at least 134° C. for at most 10 minutes, or for at most 7 minutes, or for at most 3 minutes. In one embodiment, the heat treatment comprises keeping the nanofibrillar cellulose hydrogel at a temperature of at most 138° C., or at most 136° C., or for at least 60 seconds, or for at least 2 minutes, or for at least 3 minutes. In one embodiment, the heat treatment comprises keeping the nanofibrillar cellulose hydrogel at a temperature of at most 138° C., or at most 136° C., for at most 10 minutes, or for at most 7 minutes, or for at most 3 minutes.

In one embodiment, the method comprises, after the heat treatment, the step of cooling the nanofibrillar cellulose hydrogel to a temperature of below 80° C. In one embodiment, the heating apparatus is configured to cool the nanofibrillar cellulose hydrogel to a temperature of below 80° C. after the heat treatment.

In one embodiment, the predetermined temperature, the pressure and the period of time are chosen such that the number of viable micro-organisms in the nanofibrillar cellulose hydrogel is reduced. In one embodiment, the predetermined temperature, the pressure and the period of time are chosen such that the number of viable micro-organisms in the nanofibrillar cellulose hydrogel is reduced by a factor of at least $10^3$, or of at least $10^6$, or of at least $10^{12}$.

In one embodiment the predetermined temperature and the period of time are chosen such that the number of viable micro-organisms in the nanofibrillar cellulose hydrogel is reduced by a factor of at least $10^3$, or of at least $10^6$, or of at least $10^{12}$.

Pharmaceutical products and medical devices may require sterility of the material or may require that the material is aseptic. As above indicated as absolute sterility cannot be verified, the statistical definition of sterility is used in practice, by using the security assurance level (SAL), defined as "the probability of a single viable micro-organism occurring in or on a product after sterilization". The expression "sterility of the hydrogel" or "sterile" should be understood in this specification, unless otherwise stated, as referring to a nanofibrillar cellulose hydrogel comprising fewer than 1 cfu (colony-forming units), or fewer than $10^{-1}$ cfu, or fewer than $10^{-2}$ cfu, or fewer than $10^{-3}$ cfu, or fewer than $10^{-4}$ cfu, or fewer than $10^{-5}$ cfu, or fewer than $10^{-6}$ cfu of a viable microorganism per gram of the nanofibrillar cellulose hydrogel. In other words, if the nanofibrillar cellulose hydrogel comprises fewer than $10^{-6}$ cfu of a viable microorganism per gram of the nanofibrillar cellulose hydrogel, there is a probability of not more than one viable microorganism in one million grams of the nanofibrillar cellulose hydrogel. A "colony-forming unit" is a term that describes the formation of a single macroscopic colony after the introduction of one or more microorganisms to microbiological growth media. One colony forming unit is expressed as 1 CFU.

In one embodiment, the predetermined temperature and period of time are chosen such that the treated nanofibrillar cellulose hydrogel comprises fewer than $10^{-3}$ cfu, or fewer than $10^{-6}$ cfu, of a viable microorganism per gram of the treated nanofibrillar cellulose hydrogel. In one embodiment, the predetermined temperature and period of time are chosen such that the treated nanofibrillar cellulose hydrogel comprises fewer than $10^3$ cfu, or fewer than $10^2$ cfu, or fewer than 1 cfu, or fewer than $10^{-3}$ cfu, or fewer than $10^{-4}$ cfu, or fewer than $10^{-6}$ cfu of a viable microorganism per gram of the treated nanofibrillar cellulose hydrogel. In one embodiment, the predetermined temperature, the predetermined pressure and period of time are chosen such that the treated nanofibrillar cellulose hydrogel comprises fewer than $10^{-3}$ cfu of a viable microorganism per gram of the treated nanofibrillar cellulose hydrogel. In one embodiment, the predetermined temperature, the predetermined pressure and period of time are chosen such that the treated nanofibrillar cellulose hydrogel comprises fewer than $10^{-6}$ cfu, of a viable microorganism per gram of the treated nanofibrillar cellulose hydrogel.

In one embodiment, the method comprises providing a nanofibrillar cellulose hydrogel having a viscosity of 2000-40000 mPa·s as measured at a 0.8% (w/w) concentration of the nanofibrillar cellulose in water with a Brookfield viscometer at a temperature of 20° C., with a vane spindle and a measuring speed of 10 rpm. In one embodiment, the method comprises providing nanofibrillar cellulose hydrogel having a viscosity of 12000-30000 mPa·s as measured at a 0.8% (w/w) concentration of the nanofibrillar cellulose in water with a Brookfield viscometer at a temperature of 20° C., with a vane spindle and a measuring speed of 10 rpm.

In one embodiment, the nanofibrillar cellulose hydrogel has a viscosity of at least 2000 mPa·s, or at least 12000 mPa·s, or at least 20000 mPa·s, or 2000-40000 mPa·s, or 12000-30000 mPa·s, or 15000-25000 mPa·s, or 20000-40000 mPa·s, as measured at a 0.8% (w/w) concentration of the nanofibrillar cellulose in water with a Brookfield viscometer at a temperature of 20° C., with a vane spindle and a measuring speed of 10 rpm.

The dry matter content (DSC) can be determined by keeping a sample in an oven at a temperature of 105° C. overnight (t=16 h) and by weighting the sample before and after it is kept in the oven. The weighting process is conducted following standard ISO 4119/1995 "Determination of stock concentration", with the difference that the time is 16 h.

The so-called Brookfield viscosity measurement can be determined in the following manner: A vane spindle (number 73) is selected and the Brookfield-viscosity measuring apparatus (Brookfield RVDV-III) is started. A sample of the nanofibrillar cellulose is diluted to a concentration of 0.8% by weight in water and mixed for 10 minutes using a propel mixer 700-800 rpm. No ultrasound mixing is used for modified grades, such as anionic nanofibrillar cellulose. The diluted sample mass is added to a 250 ml beaker and the temperature is adjusted to 20° C.±1° C., heated if necessary and mixed. The spindle is inserted in the beaker and measuring is started. The program registers 300 points starting with 0.5 rpm speed, then 300 points with 5 rpm and 10 rpm, and 100 points with 50 rpm and 100 rpm speeds. Relative viscosity is measured from each sample mass twice. Mean value and standard deviation are calculated for each sample, from results obtained from parallel measurements during last 5 seconds.

In one embodiment, the method comprises providing a nanofibrillar cellulose hydrogel with a turbidity value of at most 200 NTU, or at most 90 NTU, or at most 40 NTU, as measured at a 0.1% (w/w) concentration of the nanofibrillar cellulose in water. In one embodiment, the method comprises providing a nanofibrillar cellulose hydrogel with a turbidity value of 1 to 200 NTU, or 1 to 90 NTU, or 10 to 40 NTU as measured at a 0.1% (w/w) concentration of the nanofibrillar cellulose in water. In one embodiment, method comprises providing a nanofibrillar cellulose hydrogel with a turbidity value of 50 to 500 NTU, or 100 to 150 NTU, as measured at a 0.1% (w/w) concentration of the nanofibrillar cellulose in water. The oxidation level as used according to the present invention has the added utility of making the nanofibrillar cellulose hydrogel obtained through fibrillation homogenous enough and fine enough to reach the above turbidity levels. Nanofibrillar cellulose hydrogel with low turbidity value is beneficial in e.g. medical applications, such as in wound healing or as spread on wounds, and in cell culture applications, such as microscoping or other optical detection applications.

A turbidometric method based on nephelometry (90° angle between light source and detector) can be used for measuring the turbidity of samples. HACH P2100 Turbidometer, with a 50 ml measuring vessel is used for turbidity measurements. The calibration of the apparatus is checked and controlled with standard calibration bottles/samples. The dry matter of the nanofibrillar cellulose sample is determined and 0.5 g of the sample, calculated as dry matter, is loaded in the measuring vessel, which is filled with tap water to 500 g and vigorously mixed by shaking for about 30 s. Without delay the aqueous mixture is divided into 5 measuring vessels, which are inserted in the turbidometer. Three measurements on each vessel are carried out. Mean value and standard deviation are calculated for each sample.

In one embodiment, the viscosity of the nanofibrillar cellulose hydrogel, after the heat treatment, differs at most 50%, or at most 30%, or at most 10%, or at most 5%, from the viscosity of the nanofibrillar cellulose hydrogel before the heat treatment, when the dry matter content of the nanofibrillar cellulose hydrogel subjected to the heat treatment is at least 0.6 weight-% and when the viscosity after the heat treatment is measured in the same dry matter content of at least 0.6 weight-%. I.e. the viscosity is measured in the same dry matter content before and after the heat treatment. The inventors of the present invention surprisingly found out that the heat treatment carried out in e.g. an autoclave, may not affect the viscosity of the this specific hydrogel in an adverse manner in view of it further use in e.g. pharmaceutical or cosmetic products, or in cell growth medium.

One manner to characterize nanofibrillar cellulose and the thus nanofibrillar cellulose hydrogel is to define both the viscosity and the turbidity. In general, up to a certain point, as the fibrillation degree increases, the viscosity increases and at the same time the turbidity decreases. However, when the fibrillation is further continued the fibrils finally break and are therefore not able to form a strong network. After this point, both the turbidity and the viscosity begin to decrease. Such grade may be called low viscosity oxidized grade. In one embodiment, the viscosity of nanofibrillar cellulose hydrogel is 2000 to 6000 mPa·s, or 2000 to 4000 mPa·s, as measured at a 0.8% (w/w) concentration of the nanofibrillar cellulose in water with a Brookfield viscometer at a temperature of 20° C., with a vane spindle and a measuring speed of 10 rpm.

In one embodiment, providing the nanofibrillar cellulose hydrogel and subjecting the nanofibrillar cellulose hydrogel to a heat treatment are carried out while maintaining aseptic conditions. In one embodiment, providing the nanofibrillar cellulose hydrogel and subjecting the nanofibrillar cellulose hydrogel to a heat treatment and/or to the step of cooling the nanofibrillar cellulose hydrogel are carried out while maintaining aseptic conditions.

In one embodiment, the oxidation unit, the reduction unit, the fibrillation unit and/or the heating unit are configured to maintain aseptic conditions. Maintaining aseptic conditions may refer to keeping the method for treating nanofibrillar cellulose hydrogel in a closed environment so that the product is transported in pipelines from one production step to the next. Ventilation air and dilution water used should be sterile. E.g. aseptic processing rooms in which air supply, materials, and/or equipment are regulated to control microbial and particle contamination can be used. In one embodiment, the "aseptic conditions" refers to the conditions of ISO 14644-1 cleanroom standard ISO 9, or ISO 8, or ISO 5, or ISO 4, or ISO 3, or ISO 2, or ISO 1. In one embodiment, before the step of subjecting the nanofibrillar cellulose hydrogel to the heat treatment, the conditions of Class ISO 8 or Class ISO 9 are maintained. After the heat treatment maintaining aseptic conditions is even more important than between the steps of providing the nanofibrillar cellulose hydrogel and of subjecting the nanofibrillar cellulose hydrogel to the heat treatment. In one embodiment, after the step of subjecting the nanofibrillar cellulose hydrogel to the heat treatment up to the step of packaging the treated nanofibrillar cellulose hydrogel, the conditions of at least Class ISO 5 are maintained.

The present invention further relates to a nanofibrillar cellulose hydrogel obtainable by the method according to the present invention.

The present invention further relates to a nanofibrillar cellulose hydrogel, wherein the nanofibrillar cellulose is oxidized nanofibrillar cellulose, wherein the oxidation has been carried out through N-oxyl mediated catalytic oxidation of cellulose-based raw material, and has at most 50 µmol of aldehyde groups per gram of dry nanofibrillar cellulose, and wherein the nanofibrillar cellulose hydrogel contains no colony-forming units of a viable micro-organism per gram of the nanofibrillar cellulose hydrogel, as measured by culturing on a growth medium, and has a viscosity of 2000-40000 mPa·s as measured at a 0.8% (w/w) concentration of the nanofibrillar cellulose in water with a Brookfield viscometer at a temperature of 20° C., with a vane spindle and a measuring speed of 10 rpm. This kind of nanofibrillar cellulose hydrogel can be produced by the method described in this specification.

In one embodiment, the nanofibrillar cellulose hydrogel contains at most $10^{-3}$ colony-forming units of a viable micro-organism per gram of nanofibrillar cellulose hydrogel, or at most $10^{-6}$ colony-forming units of a viable micro-organism per gram of nanofibrillar cellulose hydrogel. In one embodiment, the treated nanofibrillar cellulose hydrogel contains at most $10^{-3}$ colony-forming units of a viable micro-organism per gram of nanofibrillar cellulose hydrogel, or at most $10^{-6}$ colony-forming units of a viable micro-organism per gram of nanofibrillar cellulose hydrogel.

The presence of viable micro-organisms in the nanofibrillar cellulose hydrogel can be determined by culturing on a growth medium. Several protocols for determining the number of colony forming units are available.

In an embodiment, the number of colony-forming units per gram of nanofibrillar cellulose hydrogel is determined by preparing a dilution series of the hydrogel and by plating the dilution series on separate Petrifilm plates (3M) for aerobic bacteria (aerobic plate count) and for yeasts and moulds. The plates for aerobic bacteria are allowed to grow at 37° C. for 2 days and the plates for yeasts and moulds at 30° C. for 3-5 days, after which the colonies are counted. The number of colony-forming units of aerobic heterotrophs are determined by culturing the sample on plate count agar at a temperature of 37° C. for three (3) days. Alternatively, the presence of yeast and/or fungus can be determined by culturing on potato dextrose agar at a temperature of 25° C. for five (5) days. Before the measurement, the samples are diluted by ten-fold. The presence of anaerobic micro-organisms can be determined by culturing on brewer anaerobic agar for anaerobic bacterial count at a temperature of 30° C. for three (3) days in anaerobic conditions. Before the measurement, the samples are diluted ten-fold.

In an embodiment, the number of colony-forming units is determined by following the standard ISO 8784-1 (Pulp, Paper and board—Microbiological examination. Part 1: Total count of bacteria, yeast and mould based on disintegration). The results are given as the number of colony-forming units per gram of the sample.

In an embodiment, the number of colony-forming units of viable micro-organism per gram of nanofibrillar cellulose hydrogel may be measured by incubating at 37° C. for 14 days following the USP XXIV Chapter 71 sterility test.

The present invention further relates to the use of a nanofibrillar cellulose hydrogel for use in therapy, wherein the nanofibrillar cellulose is oxidized nanofibrillar cellulose, wherein the oxidation has been carried out through N-oxyl mediated catalytic oxidation of cellulose-based raw material, and has at most 50 µmol of aldehyde groups per gram of dry nanofibrillar cellulose, and wherein the nanofibrillar cellulose hydrogel contains at most $10^{-1}$ colony-forming units of a viable micro-organism per gram of the nanofibrillar cellulose hydrogel, and has a viscosity of 2000-40000 mPa·s as measured at a 0.8% (w/w) concentration of the nanofibrillar cellulose in water with a Brookfield viscometer at a temperature of 20° C., with a vane spindle and a measuring speed of 10 rpm. In one embodiment of the nanofibrillar cellulose hydrogel for use in therapy, the nanofibrillar cellulose hydrogel contains at most $10^{-3}$, or at most $10^{-6}$, colony-forming units of a viable micro-organism per gram of the nanofibrillar cellulose hydrogel.

The present invention further relates to a nanofibrillar cellulose hydrogel obtainable by the method according to the present invention for use in therapy.

The present invention further relates to the use of a nanofibrillar cellulose hydrogel in a cosmetic product, wherein the nanofibrillar cellulose is oxidized nanofibrillar cellulose, wherein the oxidation has been carried out through N-oxyl mediated catalytic oxidation of cellulose-based raw material, and has at most 50 µmol of aldehyde groups per gram of dry nanofibrillar cellulose, and wherein the nanofibrillar cellulose hydrogel contains no colony-forming units of a viable micro-organism per gram of the nanofibrillar cellulose hydrogel, as measured by culturing on a growth medium, and has a viscosity of 2000-40000 mPa·s as measured at a 0.8% (w/w) concentration of the nanofibrillar cellulose in water with a Brookfield viscometer at a temperature of 20° C., with a vane spindle and a measuring speed of 10 rpm.

The present invention further relates to the use of a nanofibrillar cellulose hydrogel obtainable by the method according to the present invention in a cosmetic product.

The present invention further relates to the use of a nanofibrillar cellulose hydrogel in cell culture, wherein the nanofibrillar cellulose is oxidized nanofibrillar cellulose, wherein the oxidation has been carried out through N-oxyl mediated catalytic oxidation of cellulose-based raw material, and has at most 50 µmol of aldehyde groups per gram of dry nanofibrillar cellulose, and wherein the nanofibrillar cellulose hydrogel contains at most $10^{-2}$ colony-forming units of a viable micro-organism per gram of the nanofibrillar cellulose hydrogel, and has a viscosity of 2000-40000 mPa·s as measured at a 0.8% (w/w) concentration of the nanofibrillar cellulose in water with a Brookfield viscometer at a temperature of 20° C., with a vane spindle and a measuring speed of 10 rpm.

The present invention further relates to the use of a nanofibrillar cellulose hydrogel obtainable by the method according to the present invention in cell culture.

In one embodiment, the nanofibrillar cellulose hydrogel, which is used in cell culture, contains at most $10^{-3}$, or at most $10^{-6}$, colony-forming units of viable micro-organism per gram of the nanofibrillar cellulose hydrogel.

The embodiments of the invention described hereinbefore may be used in any combination with each other. Several of the embodiments may be combined together to form a further embodiment of the invention. A method, a hydrogel, a system, or a use, to which the invention is related, may comprise at least one of the embodiments of the invention described hereinbefore.

An advantage of the method according to the present invention is that the nanofibrillar cellulose hydrogel can be treated in order to reduce the number of viable micro-organisms therein without compromising, in an adverse extent, other properties such as viscosity thereof. An advantage of the method according to the present invention is that a nanofibrillar cellulose hydrogel can be provided that is able to withstand adverse effects of autoclaving on e.g. the viscosity of the hydrogel.

An advantage of the method according to the present invention is that the heat treatment can easily be combined with the step of providing the nanofibrillar cellulose hydrogel as well as e.g. the packaging step thereof following the heat treatment.

An advantage of the method according to the present invention is that a nanofibrillar cellulose hydrogel can be provided for use in pharmaceutical or cosmetic applications. An advantage of the method according to the present invention is that biocides are not needed to reduce the number of viable micro-organisms in the nanofibrillar cellulose hydrogel. In some cases, depending on the end-use of the treated nanofibrillar cellulose hydrogel, a minor amount of biocide can be used in order to reach a required purity level.

EXAMPLES

Reference will now be made in detail to the embodiments of the present invention, an example of which is illustrated in the accompanying drawing.

The description below discloses some embodiments of the invention in such a detail that a person skilled in the art is able to utilize the invention based on the disclosure. Not all steps of the embodiments are discussed in detail, as many of the steps will be obvious for the person skilled in the art based on this specification.

For reasons of simplicity, item numbers will be maintained in the following exemplary embodiments in the case of repeating components.

Figure 1:
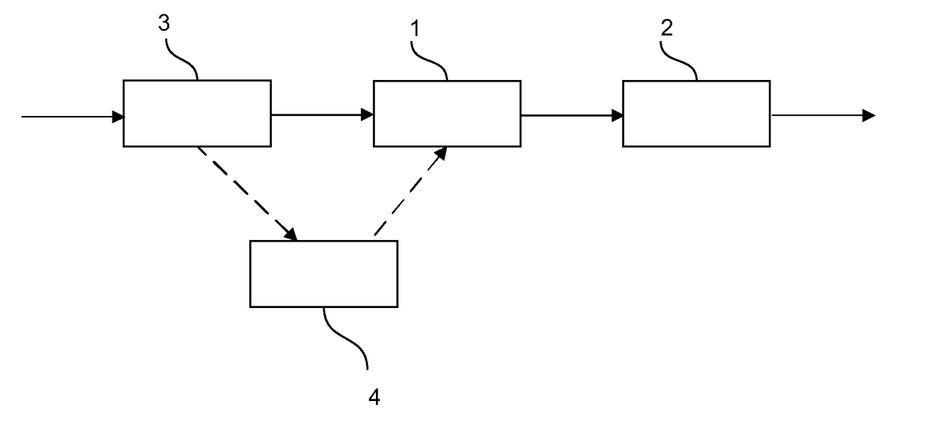

FIG. 1 illustrates a system according to one embodiment of the present invention for treating a nanofibrillar cellulose hydrogel.

In this embodiment, the system comprises an oxidation unit, in which cellulose-based raw material is subjected to an oxidation process through N-oxyl mediated catalytic oxidation. The oxidation process can be carried out as above described by using a one-step process or a two-step process.

Alternatively, the system may, in addition to the oxidation unit 3 comprise a reduction unit 4 for subjecting oxidized cellulose-based raw material to a reduction process. The alternative process, carried out with the reduction unit 4 is indicated in FIG. 1 with broken line arrows. The reduction process may alternatively be carried out in the oxidation unit 3.

As a result of the oxidation process or alternatively the oxidation and reduction processes, the cellulose-based raw material is to contain at most 50 µmol of aldehyde groups per gram of dry cellulose-based raw material.

The oxidized cellulose-based raw material is then fibrillated in a fibrillation unit 1 for providing a nanofibrillar cellulose hydrogel. The fibrillation unit is configured to fibrillate oxidized cellulose-based raw material. The oxidized cellulose-based raw material can be e.g. oxidized cellulose pulp, which is disintegrated in e.g. a fluidizer or homogenizer.

The produced nanofibrillar cellulose hydrogel is then provided into a heating apparatus 2, in which it is subjected to a heat treatment. The heating apparatus 2 is configured to keep the nanofibrillar cellulose hydrogel at a predetermined temperature within the range of 100-150° C., and at a predetermined pressure for a period of time in the range of 1 second to 180 minutes. The pre-determined temperature, the pressure and the period of time are chosen such that the number of viable micro-organisms in the nanofibrillar cellulose hydrogel is reduced, e.g. by a factor of at least $10^3$.

After the heat treatment, the nanofibrillar cellulose hydrogel is allowed to cool to a temperature of below 80° C. The treated nanofibrillar cellulose hydrogel can thereafter be packed for storage or for further use.

Example 1—Subjecting Oxidized Nanofibrillar Cellullose Hydrogel to Heat Treatment in an Autoclave In this example the effect of heat treatment carried out by autoclaving oxidized nanofibrillar cellulose hydrogel was tested.

Firstly, bleached birch pulp (bale pulp slushed to 4% consistency) was oxidized by a two-stage process. In the first step nitroxyl catalyst (TEMPO 2 mM, 2 mmol/l) was activated with NaBr (0.4 mM, 0.4 mmol/l) and NaOCl (3 mmol/g of pulp) was used as the main oxidant. The pH in the first phase was about 10 and the temperature was 25° C. The reaction proceeded rapidly and partly produced aldehyde groups. When the first step had proceeded to a desired conversion degree, the first step was stopped.

The partly oxidized cellulose was then washed and the second step was performed in a reaction medium where the pH was 3 and the temperature was 50° C.

The stop point of the first step can be chosen according to the consumption of the main oxidant or any other way. Alternatively, the pH of the reaction medium of the first step can be lowered directly to the pH range of the second step at the stop point. When the pH is lowered, chlorite, for example $NaClO_2$, is added to the reaction medium.

In this second step, the remaining aldehyde groups were rapidly oxidized to carboxyl groups with $NaClO_2$ (0.5 mmol $NaClO_2$/g of pulp) as the main oxidant. Dimethyl sulfoxide (DMSO) was used in the reaction medium in the second step to eliminate the formation of hypochlorite from chlorite.

The cellulose pulp was oxidized to a final oxidation level of 1100 μmol COOH/g pulp. The sample did not contain aldehyde groups.

After the oxidation treatment, the pulp was fibrillated to produce nanofibrillar cellulose hydrogel. The following sample dilutions were tested.

TABLE 1

Sample dilutions

| Sample | Grade | Dry matter | Notes |
|---|---|---|---|
| A | two stage, 1100 μmol COOH/g | 1.71% | — |
| B | | 1.03% | Diluted with demi-water, Bamix 30 sec |

The viscosity of the formed nanofibrillar cellulose hydrogel was determined by measuring the Brookfield viscosity at 10 rpm in a manner as above described. The results are shown in table 2.

The samples were packed in 60 ml or 175 ml bottles, and they were subjected to heat treatment by autoclaving at a temperature of 121° C. and a pressure of 215-225 kPa for 15 minutes or at a temperature of 134° C. and a pressure of 335 kPA for 3 minutes.

In addition to the samples, a control vessel filled with water was placed inside the autoclave. A temperature sensor was placed in the control vessel. The control vessel was of the same size as the actual vessels. The temperature of the control vessel was followed and when the target temperature was reached the actual autoclaving period started. After the adjusted time had passed, cooling was started. The pressure was dropped so that the boiling point was just above the control water temperature. Pressure drop was stopped at p=150 kPa, where it was held until the water temperature in the control vessel was T=80° C. After that pressure was dropped to atmospheric pressure and the autoclave could be opened and bottles removed.

The viscosity of the treated samples was determined directly from the bottles by measuring the Brookfield viscosity at 10 rpm in a manner as above described. The results are shown in table 2.

TABLE 2

| | | | Brookfield viscosities | | | | | |
|---|---|---|---|---|---|---|---|---|
| | | | 60 ml | | | 175 ml | | |
| | | | Viscosity (mPas) | | | | Viscosity (mPas) | |
| | Sample | DSC | Initial | After (Difference in %) | Sample | DSC | Initial | After (Difference in %) |
| 121° C. 15 min | A | 1.71% | 31600 | 28600 (−9%) | B | 1.03% | 10700 | 11900 (+11%) |
| | | | | | A | 1.71% | 30700 | 29825 (−3%) |

From the results it can be seen that nanofibrillar cellulose hydrogel, in which the nanofibrillar cellulose is oxidized nanofibrillar cellulose having essentially no aldehyde groups present, has its viscosity on a high level even after autoclaving, which indicates that the nanofibrillar cellulose hydrogel has a good temperature tolerance.

It is obvious to a person skilled in the art that with the advancement of technology, the basic idea of the invention may be implemented in various ways. The invention and its embodiments are thus not limited to the examples described above; instead they may vary within the scope of the claims.

The invention claimed is:

1. A method for treating a nanofibrillar cellulose hydrogel, wherein the method comprises the steps of:
providing a nanofibrillar cellulose hydrogel having a dry-matter content of at least 0.6 weight-%, wherein the nanofibrillar cellulose is oxidized nanofibrillar cellulose, wherein the oxidation has been carried out through N-oxyl mediated catalytic oxidation of cellulose-based raw material, and has at most 50 μmol of aldehyde groups per gram of dry nanofibrillar cellulose; and
subjecting the nanofibrillar cellulose hydrogel to a heat treatment, wherein the heat treatment comprises keeping the nanofibrillar cellulose hydrogel at a predetermined temperature within the range of 100-150° C., for a period of time in the range of 1 second to 180 minutes, wherein the predetermined temperature and the period of time are chosen such that the number of viable micro-organisms in the nanofibrillar cellulose hydrogel is reduced,
wherein the nanofibrillar cellulose hydrogel after the heat treatment has a viscosity of 2000-40000 mPa·s as measured at a 0.8% (w/w) concentration of the nanofibrillar cellulose in water with a Brookfield viscometer at a temperature of 20° C., with a vane spindle and a measuring speed of 10 rpm, the viscosity of the nanofibrillar cellulose hydrogel after the heat treatment differing at most by 30% from the viscosity of the nanofibrillar cellulose hydrogel before the heat treatment.

2. The method of claim 1, wherein the step of providing a nanofibrillar cellulose hydrogel comprises providing oxidized nanofibrillar cellulose, which has at most 40 μmol of aldehyde groups per gram of dry nanofibrillar cellulose.

3. The method of claim 1, wherein the step of providing a nanofibrillar cellulose hydrogel comprises providing oxidized nanofibrillar cellulose containing essentially no aldehyde groups.

4. The method of claim 1, wherein the step of providing a nanofibrillar cellulose hydrogel comprises fibrillating oxidized cellulose-based raw material to form nanofibrillar cellulose hydrogel.

5. The method of claim 1, further comprising providing a nanofibrillar cellulose hydrogel with a turbidity value of at most 200 NTU as measured at a 0.1% (w/w) concentration of the nanofibrillar cellulose in water.

6. The method of claim 1, wherein the pre-determined temperature and the period of time are chosen such that the nanofibrillar cellulose hydrogel is kept at a temperature for a period of time that correspond to a steam autoclave treatment carried out at a temperature of 121° C for 20 minutes.

7. The method of claim 1, wherein the predetermined temperature and the period of time are chosen such that the number of viable micro-organisms in the nanofibrillar cellulose hydrogel is reduced by a factor of at least $10^3$.

8. The method of claim 1, wherein the predetermined temperature and period of time are chosen such that the treated nanofibrillar cellulose hydrogel comprises fewer than $10^{-3}$ colony-forming units of a viable microorganism per gram of the treated nanofibrillar cellulose hydrogel.

9. The method of claim 1, wherein the viscosity of the nanofibrillar cellulose hydrogel, after the heat treatment, differs at most by 50%, or at most 30% from the viscosity of the nanofibrillar cellulose hydrogel before the heat treatment, when the dry matter content of the nanofibrillar cellulose hydrogel subjected to the heat treatment is at least 0.6 weight-% and when the viscosity after the heat treatment is measured in the same dry matter content of at least 0.6 weight-%.

10. The method of claim 1, wherein providing the nanofibrillar cellulose hydrogel and subjecting the nanofibrillar cellulose hydrogel to a heat treatment are carried out while maintaining aseptic conditions.

11. The method of claim 1, wherein the viscosity of the nanofibrillar cellulose hydrogel after heat treatment differs at most by 10% from the viscosity of the nanofibrillar cellulose hydrogel before the heat treatment.

12. The method of claim 1, wherein the viscosity of the nanofibrillar cellulose hydrogel after heat treatment differs at most by 5% from the viscosity of the nanofibrillar cellulose hydrogel before the heat treatment.

13. A nanofibrillar cellulose hydrogel obtainable by the method of claim 1.

14. A nanofibrillar cellulose hydrogel, wherein the nanofibrillar cellulose is oxidized nanofibrillar cellulose, wherein the oxidation has been carried out through N-oxyl mediated catalytic oxidation of cellulose-based raw material, wherein the nanofibrillar cellulose hydrogel has been subjected to a heat treatment comprising keeping the nanofibrillar cellulose hydrogel at a predetermined temperature within the range of 100-150° C., for a period of time in the range of 1 second to 180 minutes, the nanofibrillar cellulose hydrogel having at most 50 μmol of aldehyde groups per gram of dry nanofibrillar cellulose, and wherein the nanofibrillar cellulose hydrogel contains no colony-forming units of a viable micro-organism per gram of the nanofibrillar cellulose hydrogel, as measured by culturing on a growth medium, and has a viscosity of 2000-40000 mPa·s as measured at a 0.8% (w/w) concentration of the nanofibrillar cellulose in water with a Brookfield viscometer at a temperature of 20° C., with a vane spindle and a measuring speed of 10 rpm, the viscosity of the nanofibrillar cellulose hydrogel after the heat treatment differing at most by 30% from the viscosity of the nanofibrillar cellulose hydrogel before the heat treatment.

15. The nanofibrillar cellulose hydrogel of claim 14, wherein the nanofibrillar cellulose hydrogel contains at most $10^{-3}$ colony-forming units of a viable micro-organism per gram of nanofibrillar cellulose hydrogel.

16. A nanofibrillar cellulose hydrogel obtainable by the method of claim 1 for use in therapy.

17. A nanofibrillar cellulose hydrogel for use in therapy, wherein the nanofibrillar cellulose is oxidized nanofibrillar cellulose, wherein the oxidation has been carried out through N-oxyl mediated catalytic oxidation of cellulose-based raw material, and wherein the nanofibrillar cellulose hydrogel has been subjected to a heat treatment comprising keeping the nanofibrillar cellulose hydrogel at a predetermined temperature within the range of 100-150° C., for a period of time in the range of 1 second to 180 minutes, the nanofibrillar cellulose hydrogel having at most 50 μmol of aldehyde groups per gram of dry nanofibrillar cellulose, and wherein the nanofibrillar cellulose hydrogel contains at most $10^{-2}$ colony-forming units of a viable micro-organism per gram of the nanofibrillar cellulose hydrogel, and has a viscosity of 2000-40000 mPa·s as measured at a 0.8% (w/w) concentration of the nanofibrillar cellulose in water with a Brookfield viscometer at a temperature of 20° C., with a vane spindle and a measuring speed of 10 rpm, the viscosity of the nanofibrillar cellulose hydrogel after the heat treatment differing at most by 30% from the viscosity of the nanofibrillar cellulose hydrogel before the heat treatment.

18. The nanofibrillar cellulose hydrogel for use as defined in claim 17, wherein the nanofibrillar cellulose hydrogel contains at most $10^{-3}$ colony-forming units of a viable micro-organism per gram of the nanofibrillar cellulose hydrogel.

\* \* \* \* \*